(12) United States Patent
Bosco et al.

(10) Patent No.: US 8,629,252 B2
(45) Date of Patent: Jan. 14, 2014

(54) POLYSACCHARIDES DERIVATISED WITH CITRIC ACID

(75) Inventors: Marco Bosco, Gorzia (IT); Luca Stucchi, Udine (IT); Fabrizio Picotti, Udine (IT); Rita Gianni, Trieste (IT)

(73) Assignee: Sigea S.R.L., Trieste (IT)

( * ) Notice: Subject to any disclaimer, the term of this patent is extended or adjusted under 35 U.S.C. 154(b) by 273 days.

(21) Appl. No.: 12/521,308

(22) PCT Filed: Dec. 18, 2007

(86) PCT No.: PCT/IB2007/003980
§ 371 (c)(1),
(2), (4) Date: Aug. 18, 2010

(87) PCT Pub. No.: WO2008/081257
PCT Pub. Date: Jul. 10, 2008

(65) Prior Publication Data
US 2010/0311687 A1 Dec. 9, 2010

(30) Foreign Application Priority Data

Dec. 29, 2006 (EP) .................................. 06425873

(51) Int. Cl.
*C08B 37/08* (2006.01)
*A01N 43/04* (2006.01)

(52) U.S. Cl.
USPC .............................................. 536/20; 514/55

(58) Field of Classification Search
None
See application file for complete search history.

(56) References Cited

U.S. PATENT DOCUMENTS

| | | | | |
|---|---|---|---|---|
| 2,486,803 | A | * 11/1949 | Schroder et al. | ............. 428/342 |
| 2,664,397 | A | * 12/1953 | Hutchinson | ................... 210/687 |
| 2,759,787 | A | 8/1956 | Touey et al. | |
| 3,097,051 | A | 7/1963 | Wade | |

FOREIGN PATENT DOCUMENTS

EP 1702606 9/2006

OTHER PUBLICATIONS

El-Tahlawy et al. Carbohydrate Polymers 63 (2006) 385-392, available online Feb. 2006.*
Ritthidej et al. International Journal of Pharmaceutics 232 (2002) 11-22.*
Gyliene et al. CHEMIJA. 2005, T. 16 Nr. 3-4, p. 7-14.*
The National Library of Medicine—Medical Subject Headings, Dextrins, 2011.*
Gaffer, M.A., "Preparation and Utilization of New Carobxyl Group Containing Cation Exchangers Based on Starch Using a Dry Reaction Method", Starch 54(5):185-192 (2002).
Van Den Boogaard, M., "Cyclodextrin-containing Supramolecular Structures From pseudo-polyrotaxanes towards molecular tubes, insulated molecular wires and topological networks", Ph.D. Thesis, University of Groningen, The Netherlands, Jan. 2003, MSC Ph.D.—thesis series Jan. 2003, ISSN 1570-1530.
Liebert et al., "Novel approach towards hydrolytically stable starch acetates for physiological applications", Reactive & Functional Polymers 68:1-11 (2008).

* cited by examiner

*Primary Examiner* — Layla Bland
(74) *Attorney, Agent, or Firm* — Porzio, Bromberg & Newman, P.C.

(57) ABSTRACT

Non-crosslinked derivatives of oligo/polysaccharides of formula

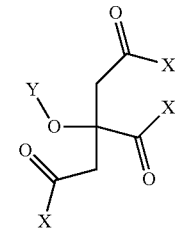

wherein:
X is OH, O⁻M, NH—R₁, O—R₁;
M is an alkaline or alkaline-earth metal, transition metal, or cation containing a quaternary nitrogen atom;
Y is H or R₂;
R1: the residue of an oligo/polysaccharide;
R2: the residue of a C1-C4 linear chain aliphatic carboxylic acid or citric acid;
provided that at least one X is NH—R1 or O—R1, while the other two X are present in acid (OH) or salified form (OM).

9 Claims, 1 Drawing Sheet

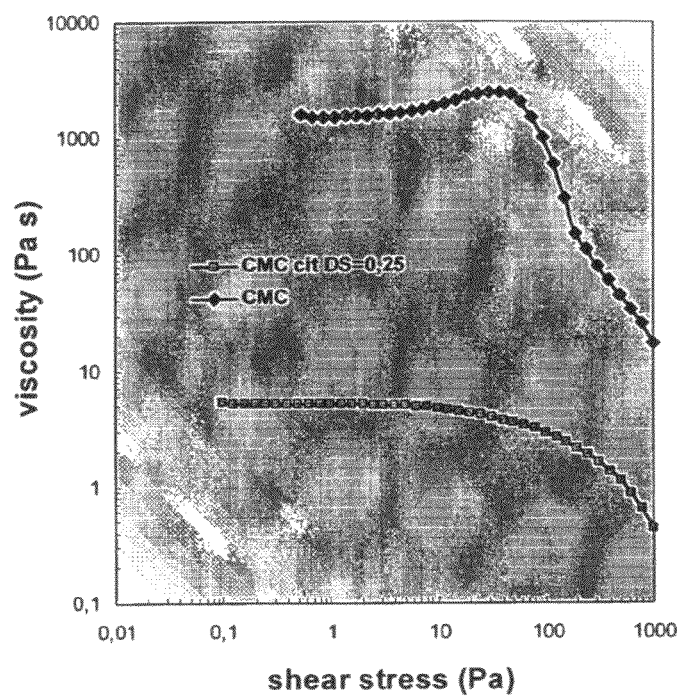
Figure shows as the investigated systems rheological curves drastically differ

POLYSACCHARIDES DERIVATISED WITH CITRIC ACID

CROSS REFERENCE TO RELATED APPLICATION

This is a National Stage of International Application PCT/M2007/003980, filed 18 Dec. 2007, which claims the benefit of Application No. 06425873.4, filed in Europe on 29 Dec. 2006, the disclosures of which Applications are incorporated by reference herein.

This invention relates to oligo/polysaccharides characterised in that they possess ester or amide bonds with citric acid, are not crosslinked in relation to the starting saccharide, and are soluble in water. The ester or amide bonds involve the carboxyl functions of citric acid and the hydroxyl or amino functions present on the starting oligo/polysaccharide.

In view of the bland, controllable conditions required for their preparation, these derivatives have well-defined, reproducible characteristics and do not present any further structural or molecular-weight modifications compared with the starting oligo/polysaccharide.

They have a very high hydratability capacity per weight unit and consequently, in the hydrated state, possess a high capacity for hydrating systems external to their contact, such as the skin systems or mucous membranes. These derivatives also manifest a modulatable ability to complex/salify metal ions such as Ag, Zn, Fe, Cu, etc. In view of these characteristics, and especially their constant composition and reproducibility, the products according to the invention can be advantageously used in the pharmaceutical and cosmetic industries as hydrating agents or constituents of pharmaceutical compositions, or as complexes/salts of metal ions such as Ag, Zn, Fe or Cu in the healing of sores. The complexes/salts can also be used as bacteriostatic/antibacterial agents.

The invention also relates to the process for their production in aqueous solution, in water/solvent, or in organic solvent only, but preferably in organic solvent. The reaction conditions, at very mild temperatures, do not degrade the oligo/polysaccharides which are homogenous in terms of degree of substitution. Moreover, the citrate residue can be esterified on the hydroxyl with a C1-C4 linear-chain aliphatic carboxylic acid or with citric acid. The invention is also directed to the obtained esters.

PRIOR ART

Processes are known wherein starch and cellulose are reacted with citric derivatives (citric acid or citric anhydride). These processes basically comprise the following steps: 1) formation of a paste or suspension of polysaccharide and citric acid, containing little or no water, in the presence of agents potentially able to induce the formation of the intermediate citrate esterifying agent (usually citric anhydride), by mixing for preset periods of time; 2) removal of water until the mixture is dry; 3) heating of the dry product at high temperatures (up to 180° C.). These stages, especially drying and heat treatment, are liable to cause extensive degradative structural changes in the initial polysaccharides (demolition of the saccharide chains with reduction of molecular weight, oxidation and elimination) and final polysaccharides (random, uncontrolled intermolecular crosslinking, etc.), and do not guarantee the constant composition and reproducibility of the final materials. However, as stated below, the use of the products obtained is designed for fields of application in which these requirements are not industrially crucial, or particularly required in regulatory terms, being sufficient meeting average characteristics (e.g. a metal-ion sequestering capacity, liquid-absorbing capacity, etc.) which are technologically acceptable, even if they vary within wide ranges; above all, they must involve low manufacturing costs, as the applications are designed for markets involving very large quantities but low added value. This latter aspect also explains why citric acid is used rather than citric anhydride, which is by far more expensive, so that its in situ formation from citric acid is preferred (with all the associated problems of composition and reproducibility mentioned above).

The uses proposed for these products are:
1. as food additives, due to their ability to prevent syneresis in frozen foods, or as dietary fibre;
2. as a heavy-metal sequestering resin in the treatment of waste water, or simply as a biodegradable ion-exchange resin.

Thus, for example, U.S. Pat. No. 2,461,139 describes the synthesis of starch derivatives using citric anhydride obtained in situ from citric acid and acetic anhydride; both a dry method and a method in alkaline aqueous suspension are used. The derivatives obtained can be used in the textile, paper and food industries.

U.S. Pat. No. 2,935,510 describes the synthesis process of acetic and propionic esters of starch in aqueous suspensions, using citric acid as crosslinking agent. These derivatives are used as additives in frozen foods.

Numerous references describe the process of derivatisation of starch with citric acid by the dry method at the temperature of 110-140° C. (Starch, 30, 1978, No. 2, pp. 47-51); these studies demonstrate that the dry process requires very precise control of the reaction parameters (temperature, etc.) to prevent excessive crosslinking (Starch, 48, 1996, No. 7/8, pp. 275-279). The dry process does not involve a high degree of substitution; DS values (the ratio between moles of citrate residues and moles of polysaccharide) of between 12.2% and 14.4% (Starch, 51, 1999, No. 10, pp. 354-361) and 16.0% (Starch, 56, 2004, pp. 364-370) are reported. Due to the persistence of the polysaccharide at high temperatures, the dry process causes partial degradation of the polymer chain and the formation of by-products (Starch, 54, 2002, pp. 185-192).

Some patents relate to derivatisation of cellulose or wood with citric acid.

U.S. Pat. No. 2,759,787 describes a dry process for the synthesis of cellulose derivatives which produces a polymer matrix insoluble in water and organic solvents; the product obtained can be used as a resin that sequesters large molecules or ions in aqueous solution. The use of citric acid as a crosslinking agent for other polysaccharides is also reported:
1. hydroxypropylmethylcellulose (Carb. Pol, 51, 2003, pp. 265-271) for the production of mechanically resistant films;
2. chitosan cross-linked with wool fibres (J. Appl. Polym. Sci, 94, 2004, pp. 1999-2007) to obtain fabrics with antimicrobial properties;
3. β-cyclodextrins bound to chitosan with a citrate bridge to obtain products with antimicrobial activity.

Many of the prior art documents imply the formation of citric anhydride, obtained by dehydration of citric acid by the action of heat (in dry processes) or following treatment with suitable desiccant agents.

EP 282289 reports the synthesis process and cosmetic use of a salt of a citric acid monoester esterified with long-chain aliphatic alcohols. Monoesters of citric acid in which the alcohol derives from carbohydrates (oligo- or polysaccharides) are not cited.

In conclusion, derivatives of citric acid with starch and cellulose have already been described, while chitosan has been used to bind cyclodextrins esterified with citric acid, acting as a bifunctional bridge.

The known products are obtained by the dry method from crude polysaccharide and citric acid at approx. 150-180° C., or in basic aqueous slurries from crude starch, citric acid and the anhydride of an organic acid. However, the products obtained by these methods present a low degree of substitution, as defined above (maximum DS=16%), and the polymer undergoes degradation effects due to the reduction of molecular weight and the formation of double bonds on the glucose units, or other collateral reactions. These effects are often unimportant for a product designed, for example, as a flocculant/sequestering agent of metal ions in waste water. The synthesis conditions are therefore designed to promote crosslinking, in order to enhance these properties.

Esters of polysaccharides with citric acid are therefore needed which have well-defined, reproducible characteristics, and whose structure is not radically different from the natural polysaccharide, so as to extend their application possibilities.

DESCRIPTION OF THE INVENTION

This invention relates to non-crosslinked, citrated, water-soluble polysaccharides which possess unexpected hygroscopicity and are useful as constituents of cosmetic or pharmaceutical formulations.

The polysaccharides according to the invention do not present irreversible structural alterations in the starting oligo/polysaccharide component (the pre-requisite for pharmaceutical and cosmetic applications) as their synthesis involves very mild conditions (ambient temperature, an inert solvent such as formamide or DMF, and activation by triethylamine under apparent pH conditions of between 6.5 and 9.0), which are therefore not degradative.

The process according to the invention also includes the synthesis and isolation of cyclic citric anhydrides wherein the hydroxyl can be esterified by known methods with C1-C4 linear-chain aliphatic carboxylic acids (formic, acetic, trifluoroacetic, dichloroacetic, trichloroacetic, propionic or butyric acid). These derivatives are then reacted with oligo/polysaccharides to give products characterised by ester or amide bonds with citric acid, absence of crosslinking and solubility in water. The ester or amide bonds involve the carboxyl functions of citric acid and the hydroxyl or amino functions present on the starting oligo/polysaccharide.

The direct use of cyclic citric anhydride under the mild conditions described allows that only one carboxyl of citric acid is bound to the saccharide residue, while the other two are present in acid or salified form.

The derivatives according to the invention have the following formula:

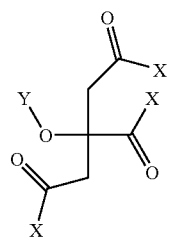

wherein:
X is OH, O⁻M, NH—R$_1$, O—R$_1$;
M is an alkaline or alkaline-earth metal, transition metal, or cation containing a quaternary nitrogen atom;
Y is H, R$_2$;
R1: the residue of an oligo/polysaccharide;
R2: the residue of a C1-C4 linear-chain aliphatic carboxylic acid or citric acid;
with the proviso that at least one X is NH—R1 or O—R1, while the other two X are present in acid (OH) or salified form (OM).

The oligo/polysaccharides are selected from chitosan, pullulan, carrageenan, or a glycosaminoglycan selected from hyaluronan, chondroitin sulphate, heparan sulphate, dermatan sulphate, keratan sulphate, low molecular weight dextrin and soluble derivatives of alkylcellulose (carboxymethylcellulose, hydroxyethylcellulose or hydroxypropylcellulose).

Said oligo/polysaccharides typically have a molecular weight between $10^3$ and $10^7$ Daltons.

The process for the preparation of the products according to the invention involves the addition of a solution containing cyclic citric anhydride or cyclic citric anhydride esterified to the hydroxyl with a C1-C4 linear-chain aliphatic carboxylic acid or citric acid, or a mixture of said citric anhydrides and a base with a solution of oligo-polysaccharide in a suitable organic solvent (formamide, dimethylformamide or dimethylsulphoxide).

Examples of bases are organic bases containing one atom of trisubstituted nitrogen, which may be aliphatic (e.g. triethylamine, DBO, DBU, DABCO or hexamine), aromatic (e.g. imidazole, pyridine or dimethylaminopyridine) or heterocyclic (e.g. pyrrolidine), an inorganic base (e.g. K$_3$PO$_4$, K$_2$HPO$_4$, potassium acetate or M$_n$CO$_3$, with M=alkaline or alkaline-earth metal), or a mixture thereof. Triethylamine is preferred.

The products according to the invention have a degree of substitution in citrate ester between 0.01 and 1.00 with respect to the repetitive unit of the saccharide, and preferably between 0.16 and 0.50.

The products according to the invention present the carboxyls in acid form or in the form of alkaline or alkaline-earth metals salts, transition metals (such as Zn, Cu and Ag) or cations with quaternary nitrogen atoms.

The products according to the invention can be used in pharmaceutical formulations, as additives for moisturising cosmetic formulations, skin care and personal hygiene, or as medical aids with a disinfectant or antibacterial action, etc., possibly suitably formulated with cationic antibiotics or antifungals.

The following examples illustrate the invention in greater detail.

EXAMPLES

The $^1$H NMR analyses are conducted in D$_2$O by Bruker Avance 400 spectrometer equipped with a 5 mm multinuclear probe with gradient z, at 300° K. The analyses also use diffusion-ordered experiments (DOSY: Diffusion Ordered Spectroscopy).

Example 1

Synthesis of Carboxymethylcellulose Citrate Ester 5.0 g of carboxymethylcellulose sodium salt was solubilised in 165 ml of formamide at 95° C. for 5 hours; the temperature was then reduced to 25° C. 3.9 g of citric anhydride, dissolved in 30 ml of formamide, and 15.0 ml of triethylamine were added. The reaction was maintained under agitation for 6 hours at 25° C. 200 ml of water was then added, and the mixture was purified by ultrafiltration. The aqueous solution was then frozen and freeze-dried. 5.3 g of lyophilisate was recovered.

10 mg of lyophilisate was solubilised in 0.7 ml of $D_2O$ and transferred to an NMR analysis tube. A DS value of 23% was obtained from integration of the methylene signals associated with citric acid (at 2.8 ppm).

Example 2

Synthesis of Chitosan Citrate Amide 316 mg of chitosan was solubilised in 35 ml of water acidified with trifluoroacetic acid at pH 3, and then freeze-dried. 457 mg of lyophilisate was recovered and redissolved in 23 ml of formamide at ambient temperature. 121 mg of citric anhydride, dissolved in 2 ml of formamide, and 230 µl of triethylamine were added. The reaction was maintained under agitation for 16 hours at 25° C. 30 ml of water was then added, and the mixture was purified by dialysis. The aqueous solution was then frozen and freeze-dried. 240 mg of lyophilisate was recovered.

10 mg of lyophilisate was solubilised in 0.7 ml of $D_2O$ and transferred to an NMR analysis tube. A DS value of 29% was obtained from integration of the methylene signals associated with citric acid (at 2.8 ppm).

Example 3

Synthesis of Pullulan Citrate Ester 125 mg of pullulan starch was solubilised in 4 ml of formamide at 80° C. for 15 minutes; the temperature was then reduced to 25° C. 121 mg of citric anhydride, dissolved in 1.5 ml of formamide, and 430 µl of triethylamine were added. The reaction was maintained under agitation for 16 hours at 25° C. 30 ml of water was then added, and the solution was neutralised to pH 7. Finally, the mixture was purified by ultrafiltration. The aqueous solution was then frozen and freeze-dried. 157 mg of lyophilisate was recovered.

10 mg of lyophilisate was solubilised in 0.7 ml of $D_2O$ and transferred to an NMR analysis tube. A DS value of 36% was obtained from integration of the methylene signals associated with citric acid (at 2.8 ppm).

Example 4

Synthesis of Hyaluronic Acid Citrate Ester 200 mg of hyaluronic acid sodium salt was solubilised in 6.6 ml of formamide at 80° C. for 4 hours; the temperature was then reduced to 25° C. 87 mg of citric anhydride, dissolved in 1.0 ml of formamide, and 278 µl of triethylamine were added. The reaction was maintained under agitation for 16 hours at 25° C. 100 ml of water was then added, and the solution was neutralised to pH 7. Finally, the mixture was purified by dialysis and ultrafiltration. The aqueous solution was then frozen and freeze-dried. 235 mg of lyophilisate was recovered.

10 mg of lyophilisate was solubilised in 0.7 ml of $D_2O$ and transferred to an NMR analysis tube. A DS value of 18% was obtained from integration of the methylene signals associated with citric acid (at 2.8 ppm).

Example 5

Synthesis of Dextrin Citrate Ester 105 mg of dextrin 10 was solubilised in 4 ml of formamide at 25° C.; 112 g of citric anhydride, dissolved in 1.5 ml of formamide, and 460 µl of triethylamine were added. The reaction was maintained under agitation for 4 hours at 25° C. The reaction mixture was then acidified with TFA and dropped into acetone under energetic agitation. The precipitate obtained was decanted, centrifuged and washed twice with 10 ml of acetone, centrifuged again, and finally dried.

10 mg of dried polysaccharide was solubilised in 0.7 ml of $D_2O$ and transferred to an NMR analysis tube. A DS value of 27% was obtained from integration of the methylene signals associated with citric acid (at 2.8 ppm).

Example 6

Preparation of a Moisturizing Cream Oil/Water

The preparation of a moisturizing cream containing a citrated polysaccharide is reported. The oil/water cream formulation contains the compound prepared in example 1, at 1% w/w concentration as moisturizing agent, mixed with excipients commonly used in dermatological cosmetics as: emulsifiers, thickening, oils, jellying, preservatives, etc.

Briefly, the preparation is made as detailed below:

600 ml of de-ionized water are added in a turbo-emulsifier (corresponding to about 60% of the total weight of the emulsion) and the oil is added under stirring at about 70° C. The mixture is emulsified and the temperature decreased up to 40° C. The volatile and thermolabile components are then added together with the water solution of CMC citrate ester prepared as described in example 1. The emulsion is left under slow stirring, warming to 25-30° C. and the final product is transferred in proper containers.

A cream with the following composition was prepared (% P/P):

| | |
|---|---|
| CMC citrate ester (Example 1) | 1 |
| Oils (palmitic and caprylic triglycerides) | 12 |
| Non-ionic Emulsifiers | 6 |
| Cetyl alchool | 2 |
| Dimethicone | 4 |
| MgAl Silicate | 2 |
| Glycerol | 3 |
| Xylitol | 2 |
| Methyl/ethyl-parabens | 0.7 |
| H2O up to a total amount of | 100 |

Example 7

Rheological Experiment

For rheological measurements carboxymethylcellulose (CMC) and citrated CMC (prepared according to example 1) aqueous systems were investigated. The tests were performed on samples dissolved in saline at the concentration of 10% w/w.

A controlled stress rheometer was used: Rheostress Haake RS150. The device was equipped with rough or smooth surfaces sensors, respectively for high or low structured systems; all measurements were done at 25° C., using a specific thermo controller.

In order to preliminarily define and compare the rheological behaviour of our systems, continuous/steady state measurements of viscosity over a wide range of shear stress (flow curves) were done.

In Figure, CMC and citrated CMC (Example 1) flow curves are shown.

Native CMC profile is peculiar of a structured system, characterized by a medium zero-shear viscosity value, an apparent increase as the applied stress increases, and a viscosity drop when a critical stress is reached. On the contrary, citrated CMC behaves like a solution, showing a low viscosity value over the whole shear stress range and little dependency on applied stress.

The invention claimed is:

1. Non-crosslinked derivatives soluble in water of

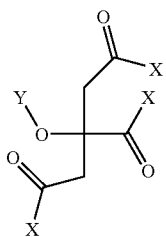

oligo/polysaccharides having formula
wherein:
X is OH, O⁻M, NH—$R_1$, O—$R_1$;
M is an alkaline or alkaline-earth metal, transition metal, or cation containing a quaternary nitrogen atom;
Y is H or $R_2$;
R1 is the residue of an oligo/polysaccharide selected from chitosan, pullulan, carrageenan, carboxymethylcellulose, hydroxyethylcellulose, hydroxypropylcellulose, or a glycosaminoglycan selected from hyaluronan, chondroitin sulphate, heparan sulphate, dermatan sulphate, and keratan sulphate;
R2 is the residue of a C1-C4 linear chain aliphatic carboxylic acid or citric acid;
with the proviso that only one X is NH—R1 or O—R1, while the other two X are present in acid (OH) or salified form (OM) having a degree of substitution in citrate ester between 0.01 and 1.00 with respect to the repetitive unit of the saccharide.

2. The derivatives as claimed in claim 1, wherein R1 is a residue of chitosan.

3. The derivatives according to claim 1, having a molecular weight of between $10^3$ and $10^7$ Daltons.

4. The derivatives as claimed in claim 1, having a degree of substitution in citrate ester between 0.16 and 0.50 per repetitive unit of the saccharide.

5. The derivatives according to claim 1, wherein the carboxyls are present in acid form or in the form of salts of alkaline or alkaline-earth metals, transition metals or cations with atoms of quaternary nitrogen.

6. Pharmaceutical compositions or medical aids comprising the derivatives claimed in claim 1, optionally mixed with suitable excipients, vehicles or actives ingredients.

7. A moisturizing cosmetic, skin care, or personal hygiene product, comprising the derivatives claimed in claim 1, mixed with suitable excipients, vehicles, or active ingredients.

8. The derivatives according to claim 1, having a molecular weight between $10^4$ and $5 \times 10^5$ Daltons.

9. Non-crosslinked derivatives soluble in water of

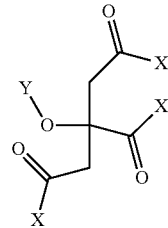

oligo/polysaccharides having formula
wherein:
X is OH, O⁻M, NH—$R_1$, O—$R_1$;
M is an alkaline or alkaline-earth metal, transition metal, or cation containing a quaternary nitrogen atom;
Y is H or $R_2$;
R1 is the residue of chitosan;
R2 is the residue of a C1-C4 linear chain aliphatic carboxylic acid or citric acid; with the proviso that only one X is NH—R1 or O—R1, while the other two X are present in acid (OH) or salified form (OM) having a degree of substitution in citrate amide between 0.01 and 1.00 with respect to the repetitive unit of chitosan.

* * * * *